(12) United States Patent
Ongaro et al.

(10) Patent No.: US 10,179,182 B2
(45) Date of Patent: Jan. 15, 2019

(54) AUTOCLAVE FOR STERILISATION

(71) Applicant: NAKANISHI INC., Tochigi (JP)

(72) Inventors: Daniele Giovanni Ongaro, Villa di Serio (IT); Maria Pia Ghilardi, Villa di Serio (IT)

(73) Assignee: NAKANISHI INC., Tochigi (JP)

( * ) Notice: Subject to any disclaimer, the term of this patent is extended or adjusted under 35 U.S.C. 154(b) by 0 days.

(21) Appl. No.: 14/767,401

(22) PCT Filed: Mar. 11, 2014

(86) PCT No.: PCT/IB2014/059626
§ 371 (c)(1),
(2) Date: Aug. 12, 2015

(87) PCT Pub. No.: WO2014/141063
PCT Pub. Date: Sep. 18, 2014

(65) Prior Publication Data
US 2016/0030608 A1    Feb. 4, 2016

(30) Foreign Application Priority Data
Mar. 12, 2013  (IT) ............................ MI2013A0374

(51) Int. Cl.
*A61L 2/07* (2006.01)
*C02F 1/28* (2006.01)
(Continued)

(52) U.S. Cl.
CPC ............... *A61L 2/07* (2013.01); *C02F 1/001* (2013.01); *C02F 1/004* (2013.01); *C02F 1/283* (2013.01);
(Continued)

(58) Field of Classification Search
CPC .. A61L 2/07; C02F 1/001; C02F 1/004; C02F 1/285; C02F 1/283
See application file for complete search history.

(56) References Cited

U.S. PATENT DOCUMENTS 3,971,338 A * 7/1976 Alexson ................. A01K 63/04
119/262
6,068,815 A * 5/2000 Oberleitner ............ A01N 37/16
134/170

(Continued)

FOREIGN PATENT DOCUMENTS

| DE | 198 60 290 A1 | 6/2000 | |
| GB | 1235952 A * | 6/1971 | ............... A61L 2/24 |
| WO | 2013/093700 A2 | 6/2013 | |

OTHER PUBLICATIONS

International Search Report, dated Aug. 14, 2014, three pages.

*Primary Examiner* — Regina M Yoo
(74) *Attorney, Agent, or Firm* — Vorys, Sater, Seymour & Pease LLP

(57) ABSTRACT

Provided is an autoclave for sterilization including a sterilization chamber, a tank of water, connection means configured to connect the tank to the sterilization chamber in a fluidic through connection, heating means configured to heat and to pressurize the water and to supply the sterilization chamber to perform sterilization cycles, in which the tank includes a filter, the tank is in addition divided into a high potential portion and a low potential portion, the portions being in reciprocal fluidic through connection through the filter, the filter comprising a plurality of filtering layers including distribution layers configured to slow down and improve the distribution of the water along the entire area of the layers and active layers configured to perform purification functions of the water.

9 Claims, 2 Drawing Sheets

(51) Int. Cl.
 *C02F 1/00* (2006.01)
 *C02F 103/00* (2006.01)
(52) U.S. Cl.
 CPC ..... *A61L 2202/24* (2013.01); *C02F 2103/006* (2013.01)

(56) References Cited

U.S. PATENT DOCUMENTS

| | | | |
|---|---|---|---|
| 6,354,310 B1* | 3/2002 | Farr | B08B 7/0021 |
| | | | 134/105 |
| 2002/0163636 A1* | 11/2002 | Oberleitner | A01N 37/16 |
| | | | 356/128 |
| 2004/0055939 A1* | 3/2004 | Wybo | B01D 29/07 |
| | | | 210/167.11 |
| 2005/0025663 A1* | 2/2005 | Burke | A61L 2/022 |
| | | | 422/28 |
| 2006/0280647 A1* | 12/2006 | Burke | A61L 2/022 |
| | | | 422/28 |
| 2014/0102965 A1* | 4/2014 | Jones | C02F 1/002 |
| | | | 210/136 |

\* cited by examiner

AUTOCLAVE FOR STERILISATION

The present invention relates to an autoclave for sterilisation of the type as recited in the preamble of the first claim.

Autoclaves of the type for medical-dental use are currently known of.

They are supplied with demineralised and sterilised water which is brought by said autoclave to high temperatures and pressures. The water in a steam state is then channelled into an insulated chamber in which the various items to be sterilised, in particular medical or medical-dental instruments, are placed.

The steam performs a sterilisation cycle, at determined temperatures and pressures, even variable, for a given amount of time after which it is expelled into the environment, possibly after cooling.

The prior art described above entails several significant drawbacks.

In particular the supply of demineralised and sterilised water is expensive and laborious for the user of the autoclave.

In addition, the dispersion of the water into the environment after the sterilisation cycle is harmful to the environment.

Yet another drawback is that the production of demineralised and sterilised water has a high energy cost.

In this situation the technical purpose of the present invention is to devise an autoclave for sterilisation able to substantially overcome the drawbacks mentioned above.

Within the sphere of said technical purpose one important aim of the invention is to devise an autoclave for sterilisation which permits a simple and economical supply of water for the sterilisation.

A further technical task of the present invention is to obtain an autoclave for sterilisation the maintenance of which is simple and safe.

A further, no less important aim of the present invention is to obtain an autoclave for sterilisation which permits an energy saving in the production of demineralised and sterilised water.

The technical purpose and specified aims are achieved by an autoclave for sterilisation as claimed in the appended claim 1. Preferred embodiments are described in the dependent claims.

Figure 1:
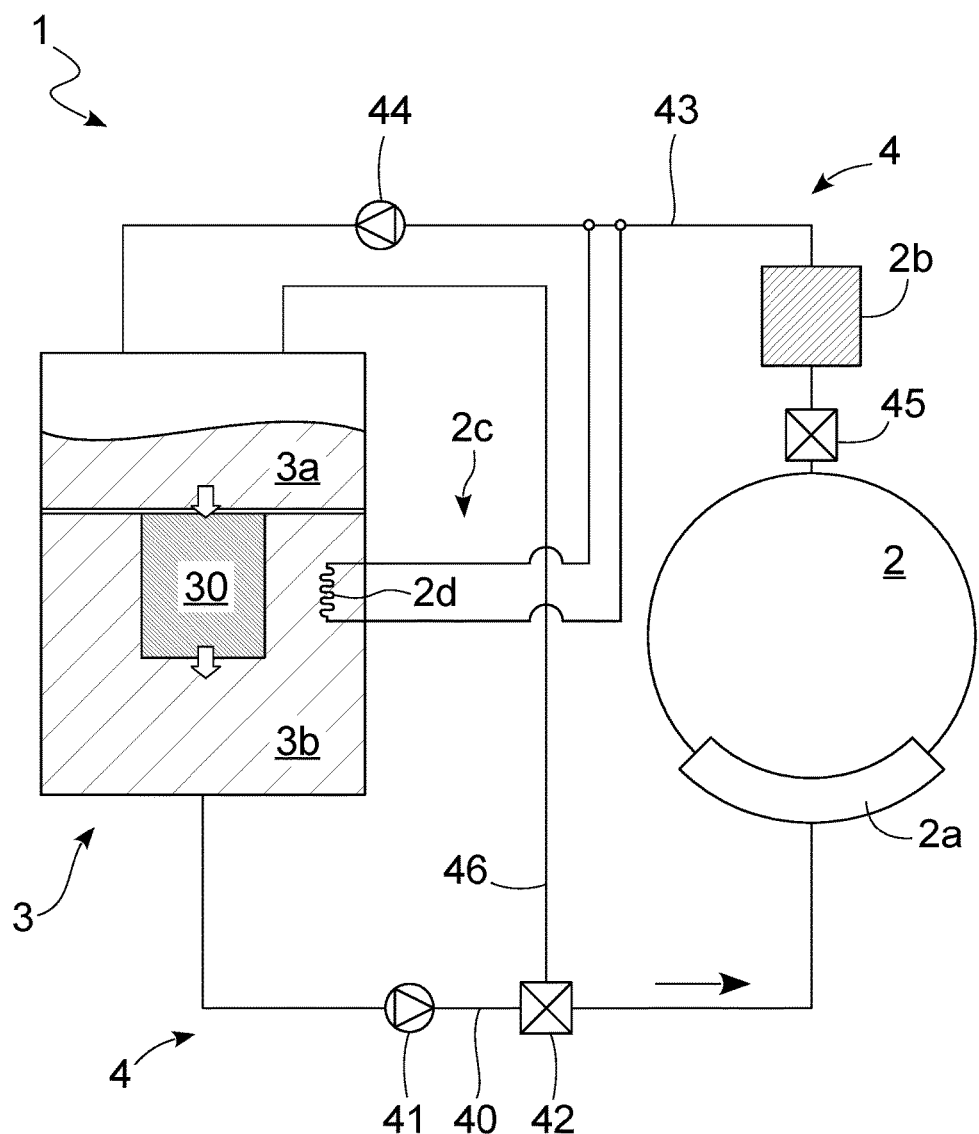
Figure 2:
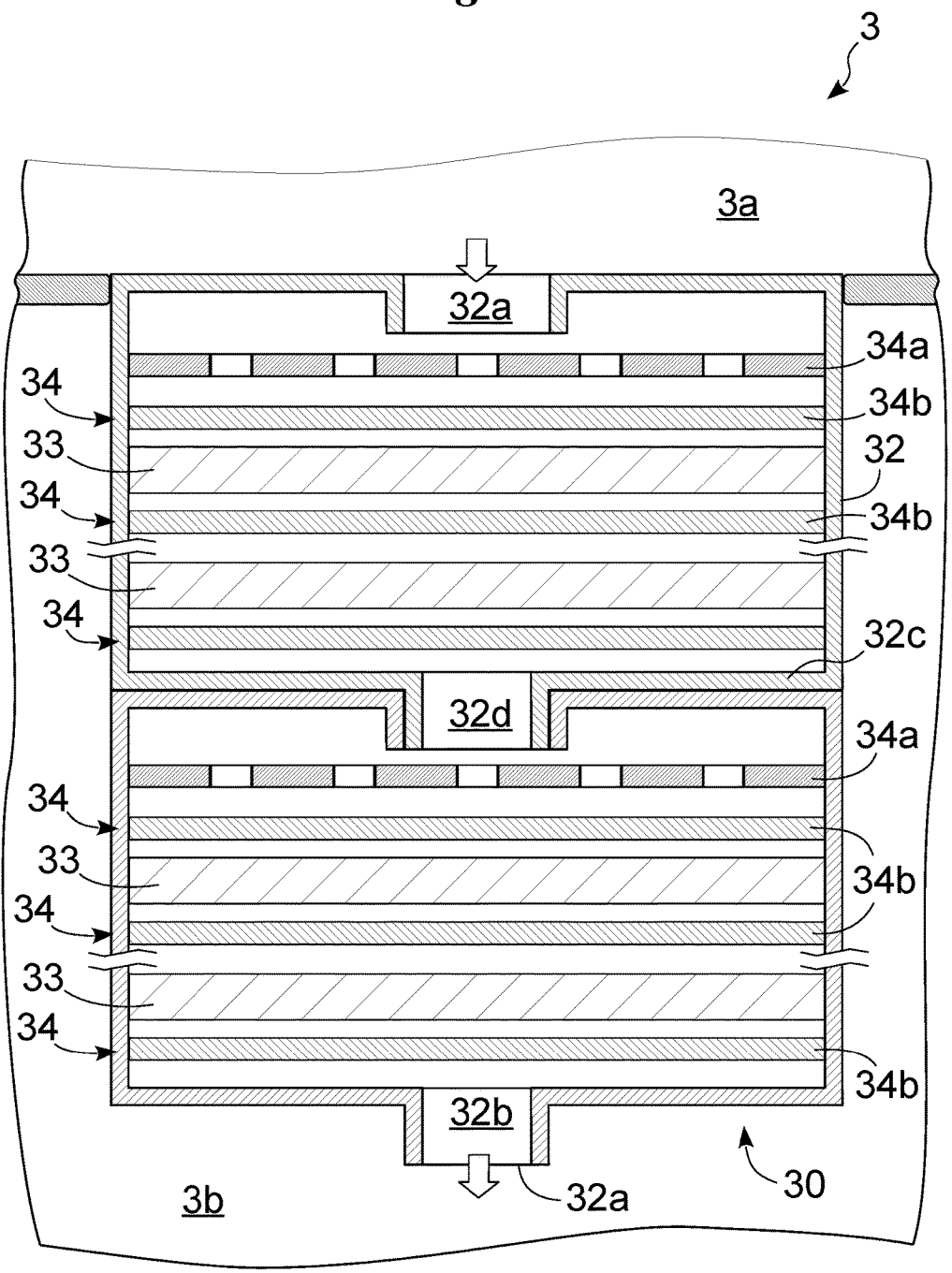

The characteristics and advantages of the invention are clearly evident from the following detailed description of a preferred embodiment thereof, with reference to the accompanying drawings, in which:

FIG. 1 shows a schematic view of the autoclave for sterilisation according to the invention; and FIG. 2 shows a portion of the autoclave for sterilisation according to the invention.

With reference to said drawings, reference numeral 1 globally denotes the autoclave for sterilisation according to the invention.

It comprises, in brief, a sterilisation chamber 2 and a water tank 3 including a purification filter 30 in fluid through connection with the sterilisation chamber.

The filter 30 is suitable to purify, and the term purify is taken to mean in the present application sterilise and/or demineralise, the water by the mere passage of said water through filtering layers. The passage of the water is achieved by a pressure gradient between different portions of the tank 3 appropriately due simply to gravitational forces.

The filter 30 is thus placed in the tank 3 in an intermediate position in relation to the pressure gradient direction, in such a way that the tank 3 is able to contain in a high potential portion 3a preferably placed in the upper part, non purified water, and in a low potential portion 3b, preferably placed in the lower part, purified water passed through the filter 30. The two portions 3a and 3b are reciprocally isolated except for the filter 30 and a possible connection provided for and described below.

The tank 3 may, in addition, comprise sensors 5 of the quality of the filtered water, preferably placed in the low potential portion 3b and consisting for example of conductivity and cloudiness sensors of the water and the like. Such sensors 5 are in addition preferably insertable and extractable from the tank 3 by means of simple, quick-fit attachments.

The filter 30 is preferably connected to the tank by means of a quick-fit coupling and includes a plurality of filtering layers 31.

In structural detail, the filter 30 (FIG. 2) is contained in a casing 32, part of the filter 30, preferably cylindrical or prismatic. The casing 32 comprises an input 32a and an output 32b preferably having a smaller area than the total area of the base of the cylinder constituting the filter 30. The input 32a and the output 32b are preferably circular and positioned in the centre of the upper and lower bases of the cylinder constituting the filter 30.

The input 32a and the output 32b constitute an obligatory passage for the water which passes, appropriately by gravity, from the high potential portion 3a to the low potential portion 3b.

The casing 32 may in addition be sub-divided into a plurality of reciprocally separable sections. In such case, the casing 32 comprises intermediate bases 32c reciprocally connected by known connection means, such as threads or the like and further comprises intermediate apertures 32d of the type similar to the input 32a and output 32b, suitable to allow the passage of water between the portions 3a and 3b. Such intermediate apertures further allow a slowing of the flow of water and easy maintenance of the filter 30 or the possibility of inserting filtering layers 31 of a smaller diameter, given that said intermediate apertures 32d define conical portions of a lesser diameter than the diameter of the casing 32 (FIG. 2).

The filtering layers 31 are suitable for entirely covering a normal cross-section in relation to the main axis of the cylindrical casing 32. In addition, given that in use the main axis of the casing 32 is preferably parallel to the direction of the gradient of potential between the portions 3a and 3b and thus preferably vertical the filtering layers are positioned on the horizontal plane.

In the functioning details, the filtering layers 31 divide mainly into two types: the active layers 33 and distribution layers 34 of the water.

The active layers 33 are each suitable to perform purification or demineralisation functions of the water. A variable number of active layers 33 may be provided for, preferably between seven and thirteen.

In particular, at least one active carbon layer 33 is provided for, and preferably a quantity between four and eight of active carbon layers and at least one active carbon layer impregnated with silver. Each of these preferably has a thickness of 1 mm to several centimeters. The main function of such layers is to eliminate chlorine and chloromethanes, to eliminate microorganisms and prevent their growth, to remove iodine and other substances. In addition, the active carbon layers 33 are preferably placed both in the upper part of the filter 30 and in the lower part of said filter 30. In fact they are suitable to eliminate most of the impurities initially present in the water and to eliminate the possible particles and impurities formed by further active layers. Such layers may also be vegetable carbon, catalytic carbon or vegetable catalytic carbon.

The active layers 33 further comprise redox compounds. These remove the inorganic contaminants from the water and neutralise the pH. From one to three layers of such type are present, these too preferably in both the lower part and the upper part. The redox compounds substantially make available positive electrons or charges. On account of this exchange of electrons, many contaminants are converted into innocuous components which do not require further treatment. Other types of contaminants are removed from the flow and fixed to the active layer 33.

Other active layers 33 may be composed of iodine particles, possibly impregnated in resins, suitable for eliminating possible micro-organisms. Such particles preferably have an uneven charge number. Preferably solely one active layer 33 of this type is provided for.

Another type of active layer 33 preferably present is a layer in anionic resin, suitable to eliminate iodine and iodides from the water and thus preferably placed under the layers with iodine particles.

Yet another type of active layer 33 preferably present is a layer in resin for ionic exchange, composed of a mixture of anionic and cationic resins and suitable to remove inorganic and radiological resins. Such active layer 33 is preferably placed near the bottom of the filter 30.

The distribution layers 34 are instead suitable for slowing down or improving the distribution along the area of the normal cross-section of the cylinder.

In particular a first type of distribution layer 34 is composed of a perforated disc 34a, that is to say a polymer disc including a plurality of holes along the entire area. It is placed at the top of the filter 30, a short distance from the input 32a or at the intermediate apertures 32d. Such layer 33 is suitable to better distribute the water in input and output.

A second type of distribution layer 34 is composed of a layer of paper 34b.

The paper layer 34b is much thinner than the other layers. It permits an optimal distribution of the flow of water along the area of the normal cross-section of the casing 32, and thus the optimisation of performance of the active filters 33. The paper layer 34b further retains the bigger impurities thus also partially acting as an active filter. Any type of paper can be used such as felt paper, nylon filter paper or other. Preferably two paper layers 34 enclose, preferably not in direct contact with, each active layer 33, except for the last active filter at the bottom of the filter 30 which obviously does not need redistribution underneath.

The active layers 33 and the distribution layers 34 are thus substantially alternated along the length of the filter 30, except at the top, where the perforated disc 34a and a paper layer 34b are consecutive.

A similar filter 30 is described in the following patent applications: US-A-2008/0302714, in particular in FIGS. 4 and 7 and from paragraph [0039] to paragraph [0108], and also in the patent applications U.S. Pat. No. 5,635,063, U.S. Pat. No. 6,572,769, U.S. Pat. No. 7,276,161, U.S. Pat. No. 7,413,663 of the company Zero Technologies, Inc. However such filters, present since the '90s are destined for domestic use and no person skilled in the art has ever supposed that they could be adapted, as regards capacity and filtering power, for use in autoclaves. However the applicant has cleverly discovered, after a long and surprising series of analyses, that said filters are adaptable to the autoclave sector The sterilisation chamber 2 is in itself known and suitable to contain objects, in particular medical or medical-dental devices. It is also suitable to withstand high pressures and internal temperatures.

It is joined to heating means 2a of the water, also in themselves known and suitable to heat and pressurise the purified water coming from the tank 3, in particular from the low potential portion 3b. In one embodiment, heating means 2a is a heater.

The sterilisation chamber 2 may in addition be joined to disposal means 2b of the high temperature steam, such as coolers, filters for expulsion into the environment of part of the steam and so forth. In particular coolers such as Peltier cells, heat exchangers and the like may be present which may be directly connected to the liquid contained in the portion 3b or in series to the duct 46. Such disposal means are preferably separated from the chamber 2 by means of a second valve 45 described below. The emptying means are then suitable to empty the steam present in the chamber 2 and also the condensed liquid present on the bottom of said chamber 2, appropriately by means of a special pump and dip tube on the bottom of the chamber 2.

It may comprise cooling means 2c suitable to permit the cooling of the fluid at high temperatures by means of its passage into the tank 3, and in particular in the low potential portion 3b. In one embodiment, cooling means 2c is a heat exchanger such as a radiator. Such solution, possible with tanks of large dimensions, can be achieved with a tube connected in input and output by means of dedicated valves inside the chamber 2 and passing, preferably by means of a coil 2d, inside the tank 3 in the low potential portion 3b. The cooling means 2c confer a further advantage consisting of the degassing of the water. The cooling means 2c are also preferably separated from the chamber 2 by means of the second valve 45. Alternatively to the coil 2d a small storage tank may also be present with appropriate emptying means which also acts as a liquid/steam separator for the vacuum pump.

The chamber 2 and tank 3 are reciprocally connected in a fluidic through connection by connection means 4, preferably composed of a series of tubes or the like.

Such connection means 4 comprise a first connection 40 suitable to connect the tank 3, and in particular the low potential portion 3b, to the chamber 2. First transfer means 41 of the fluid from the tank 3 to the chamber 2 are also provided for along the first connection, preferably composed of a pump or of a suitable arrangement of the elements which can exploit the gravitational gradient for said transfer. The first connection 40 further comprises a first valve 42, suitable to interrupt or restore the first connection 40 on command.

The connection means 4 further comprise a second connection 43 suitable to connect the chamber 2 to the tank 3, and in particular to the high potential portion 3a. Second transfer means 44 of the fluid from the chamber 2 to the tank 3 are also provided for along the second connection, preferably composed of a pump. The second connection 43 further comprises a second valve 45, previously mentioned and suitable to interrupt or restore the second connection 43 on command.

The second connection 43 may interface or be connected to the disposal means 2b.

Alternatively the disposal means 2b may directly dispose of the water without passing back through the tank 3 and thus without the autoclave 1 comprising the second connection 43.

Lastly, the connection means 4 also preferably comprise a third connection 46 suitable to connect the low potential portion 3b of the tank 3 to the high potential portion 3a of said tank 3. Third transfer means of the fluid from the low potential portion 3b of the tank 3 to the high potential portion 3a are provided along the third connection, preferably comprised of a pump. The third connection 46 further comprises a third valve, suitable to interrupt or restore the third connection 46 on command. Said third valve is preferably structurally integrated with the first valve 42. In this case the first valve 42 is a three-way valve suitable at least to connect the low potential portion 3b of the tank 3 alternatively to the chamber 2 or to the high potential portion 3a of said tank 3. The third connection 46 too may partly coincide with the first connection 40, as illustrated in FIG. 1, as also the third transfer means coincide with the first transfer means 41.

The third connection 46 is suitable to permit a recirculation of the water and to prevent the chemical-biological deterioration of the stagnant water.

The functioning of the autoclave 1, described above in structural terms, is as follows.

The water is introduced into the high potential portion 3a of the tank 3, preferably directly from a tap of running water or the like.

The water crosses the filter 30 with the various membranes preferably by falling, and is thus purified, that is to say demineralised and sterilised.

The pure water falls inside the low potential portion 3b of the tank 3 and is stored therein. It subsequently crosses the first connection 40 and is channelled by the first transfer means 41 through the first three-way valve 42 to the sterilisation chamber 2.

Should the chamber 2 not require further water, the first three-way valve 42 connects the low potential portion 3b of the tank 3 to the high potential portion 3a of said tank 3, activating the advantageous recirculation of the water. The first transfer means 41 are in addition timed so as not to circulate continuously in any case so as not to overload the filter 30.

Before reaching the sterilisation chamber 2 the water is intercepted by the heating means 2a which heat and pressurise the water and introduce it into the chamber 2 realising the sterilisation cycles provided for of the instruments therein.

At the end of sterilisation the steam comes out of the chamber 2, is channelled through the disposal means 2b is cooled to temperatures below 40° C. and is re-introduced, through the second connection 43 and by means of the second transfer means 44 and the second valve 45 to the high potential portion 3a of the tank 3.

In this step the steam may also be cooled by the cooling means 2c, which may be in series or in parallel with other coolers and/or with the various tubes.

Should the sensors 5 signal that the pure water has a cloudiness or conductivity above the predefined parameters, the machine signals that cleaning or rapid re-placement of the filter is needed.

The autoclave for sterilisation 1 achieves important advantages.

In particular, the water is supplied directly from running water and seldom, given that the autoclave 1 permits continuous recirculation. This latter advantage further permits a reduced environmental impact of the invention and eliminates the cost of demineralised water.

The tank 3 containing the filter 30 may in addition be used with autoclaves already present on the market and in medical dental practices, so as to permit an extremely simple improvement thereof.

The invention claimed is:

1. An autoclave for sterilisation, comprising:
   a sterilisation chamber;
   a tank of water;
   connection means configured to connect said tank to said sterilisation chamber in a fluidic communication; and
   a heater configured to heat and to pressurise said water and to supply said sterilisation chamber with said water to perform sterilisation cycles, said tank comprising a filter, said tank being divided into a high potential portion and a low potential portion, said high potential and low potential portions being in reciprocal fluidic communication through said filter and the potential of said water within said high potential and low potential portions is achieved by gravity, said filter comprising a plurality of filtering layers comprising distribution layers configured to slow down and improve the distribution of the water along the entire area of said plurality of filtering layers and active layers configured to perform purification of said water.

2. The autoclave of claim 1, wherein said connection means comprises a first connection configured to connect said low potential portion to said sterilisation chamber and a second connection, configured to connect said sterilisation chamber to said high potential portion.

3. The autoclave of claim 2, wherein said connection means further comprises a third connection configured to connect said low potential portion to said high potential portion and a pump configured to transfer the water from said low potential portion to said high potential portion so as to achieve recirculation of the water.

4. The autoclave of claim 1, wherein said sterilisation chamber comprises a radiator configured to permit the cooling of the water by mean of a passage through said tank.

5. The autoclave of claim 1, wherein said distribution layers and active layers are substantially alternated.

6. The autoclave of claim 1, wherein said active layers comprise a plurality of active carbon active layers.

7. The autoclave of claim 1, wherein said active layers comprise at least one active layer made from redox compounds.

8. The autoclave of claim 1, wherein said distribution layers comprise a layer of paper.

9. The autoclave of claim 1, wherein said distribution layers comprise at least one distribution layer composed of a perforated disc.

\* \* \* \* \*